Feb. 4, 1975 R. YOSHIMURA Plant Pat. 3,679
AZALEA PLANT
Filed Aug. 2, 1973
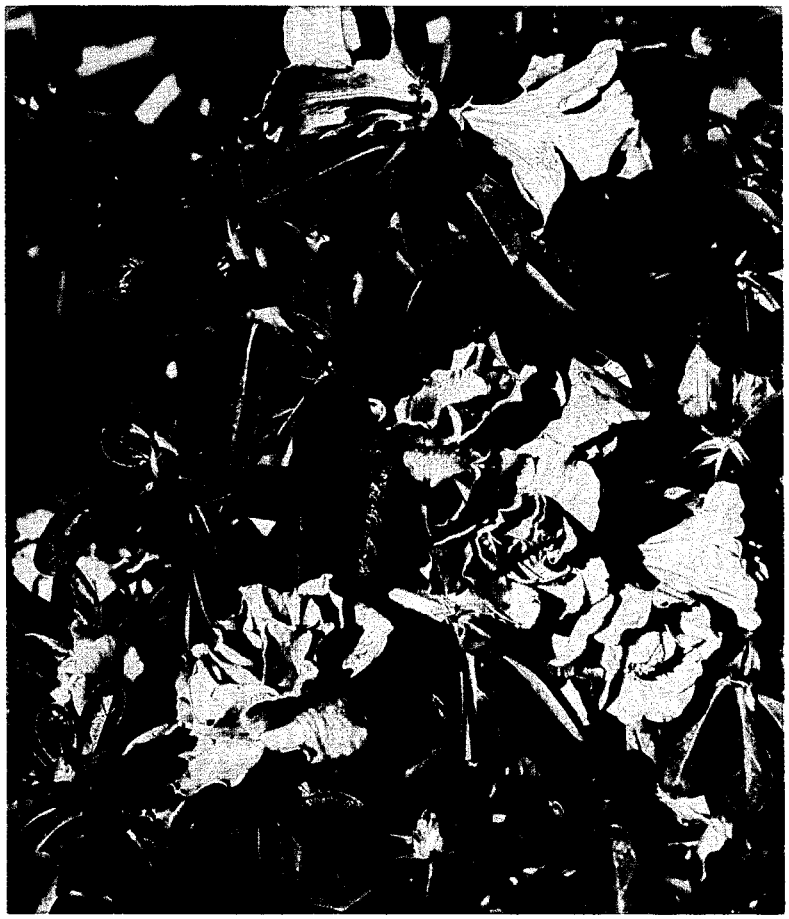

United States Patent Office

Plant Pat. 3,679
Patented Feb. 4, 1975

3,679
AZALEA PLANT

Raymond Yoshimura, 827 S. Gladys,
San Gabriel, Calif. 91772

Filed Aug. 2, 1973, Ser. No. 385,073
Int. Cl. A01h 5/00
U.S. Cl. Plt.—57 1 Claim

ABSTRACT OF THE DISCLOSURE

This invention relates to a new and distinct variety of azalea plant.

This plant resulted from the cross breeding of an azalea plant known in the trade a Avenir, a Beligian hybrid that is not patented, with the azalea plant known in the trade as Chimes, also a non-patented variety. The original plant was produced by me in 1956 at San Gabriel, Calif. using Avenir as the seed parent and Chimes as the pollen parent.

The flowers produced by the new variety are substantially campanulate in configuration and are predominantly double with a few flowers being semi-double. The flowers are a reddish rose in color. The peak blooming period of this variety normally occurs in March and April in the coastal regions of southern California. The plant is a vigorous semi-upright shrub.

Compared to its seed parent Avenir, which bears salmon pink blooms, the flowers produced by the new variety are rose red, are smaller in size than the large double flowers produced by the seed parent, the flowers of the new variety are double with an occasional semi-double appearing on the bush, and appear to last longer on the plant than those produced by the seed parent.

Compared to its pollen parent Chimes, the flowers of the new variety are Delft Rose in color with Garnet Lake spots or dots whereas those of the pollen parent are a reddish orange in color. The blooms of Chimes are usually single whereas those of the new variety are double and semi-double.

The new variety is generally grown as a semi-upright bush and does not train very well as a tree. The plant has been reproduced by cuttings and grafting performed by me at San Gabriel, Calif. The numerous reproductions produced from the new variety all bear the distinguishing characteristics of the new variety and prove that the strain is true when asexually produced in the above manner; this variety cannot be reproduced true from seed.

The accompanying drawings in full color show a typical specimen of the blooms and foliage. The colors are as true as it is possible to reproduce them by this type of color representation. A detailed description of the new variety of azalea plant follows and to facilitate identification of the important colors described in the specification, the designations adopted by the British Horticultural Colour Charts has been followed.

THE FLOWER

Locality where grown and observed: San Gabriel, Calif.

Flowers borne: A number of flowers are borne on a stem.

Continuity: The plant blooms sporadically throughout the year depending on climatic conditions but the peak blooming period in the coastal regions of southern California occurs normally in March and April at which time the bush will bear a profusion of blooms. Flowers are on the plant from six to eight weeks during cooler weather but their presence is considerably shorter during warmer weather.

Bud:

*Before calyx opens.*—Size: About three eighths of an inch in diameter and from one half to three quarters of an inch in length.

*As calyx breaks.*—Color: Predominantly green. Sepals: Shape: substantially elliptic. Size: Vary from one half to three quarters of an inch in length.

As first petal opens:

*Size.*—One and one half to one and three quarters inches in length with the width being slightly less.

*Color.*—The color is predominantly Delft Rose o20/1 and sometimes Delft Rose o20.

*Shape.*—The petals appear to be substantially round with the margin undulate. The petals arrange themselves compactly around the base opening up more toward the tip.

Bloom:

*Size.*—The blooms are from two and one half to three inches at the widest diameter.

*Petalage.*—There are fifteen or more petals to a bloom.

*Form.*—The bloom is substantially campanulate, opening quite wide at the outer end.

*Petals.*—The petals are substantially orbicular at the outer end and become slightly pointed or more obtuse at the base. The margin of each petal is usually undulate.

*Color.*—The predominant color is between Delft Rose o20/1 and Delft Rose o20. The petals have dots that are Garnet Lake $_8$28.

*General color effect.*—The general color effect is Delft Rose o20/1.

*Flower longevity.*—The blooms last up to eight weeks during cooler weather and only three weeks during warmer weather.

REPRODUCTIVE ORGANS

Stamens: This plant has only one stamen to each bloom.

Filaments: There is only one filament present.

Anthers: There are no anthers visible.

Pistil: Each flower appears to have only one pistil which includes the stigma and ovary, the style is not very prominent. Color: The stigma is from medium to dark red.

THE PLANT

Foliage:

*Leaves.*—Leaves are broadly elliptic with the tip apiculate and the base attenuate. Margins of the leaves are slightly ciliate. The surface of the leaves is slightly puberulent and the leaves are alternately arranged.

*Petiole.*—The petiole is usually a quarter of an inch long.

*Veins.*—Veins are pinnately arranged and are more prominent on the under side of the leaf than on the upper side. The back of the petiole and the main veins is strigose.

*Size of leaves.*—The leaves are from one and one eighth to one and three eighths inches in width and from two and one eighth to two and three eighths inches in length when mature. The ratio of length to width of the leaves of the new variety appears to be greater than the corresponding ratio of length to width in the parent plants.

*Color of leaves.*—Upper side of leaf: Ivy Green $ooo_{10}$60/3. Under side of leaf: Between Spinach Green o960/3 and o960/2.

Growth habit: The new variety is classed as a moderate grower. The new plants will grow from six to eight inches in one year. The plant usually attains a maximum height of three feet and since it is semi-upright it will have a spread of approximately three feet. This variety is predominantly a bush of the semi-upright type.

Main stems: The main stems can be up to one inch in dameter.

Having described my invention, I claim:

1. The new and distinct variety of azalea plant substantially as herein shown and described, characterized particularly as to novelty by the double, campanulate, predominantly Delft Rose blooms that have Garnet Lake dots borne in great profusion during cooler weather with many blooms on a stem, by its medium semi-upright growth habit, and by the dark green leaves that are wider compared to the length of the leaves than those of its parent plants.

No references cited.

ROBERT E. BAGWILL, Primary Examiner